: Patent Number: 5,056,514
Date of Patent: Oct. 15, 1991

United States Patent [19]
DuPont

[54] ENDOTRACHEAL STETHOSCOPE

[76] Inventor: Frank DuPont, 4495 Clarke Drive, St. Clair, Mich. 48079

[21] Appl. No.: 428,892

[22] Filed: Oct. 30, 1989

[51] Int. Cl.$^5$ ............................................. A61M 16/00
[52] U.S. Cl. ........................... 128/207.14; 128/204.23; 128/207.15
[58] Field of Search ....................... 128/204.23, 207.14, 128/207.15, 642, 671, 715, 773, 911; 181/131

[56]     References Cited
U.S. PATENT DOCUMENTS

| | | | |
|---|---|---|---|
| 3,493,075 | 2/1970 | Mendelson et al. | 181/131 |
| 3,499,435 | 3/1970 | Rockwell et al. | 128/671 |
| 3,734,094 | 5/1973 | Calinog | 128/642 |
| 4,198,963 | 4/1980 | Baskalow et al. | 128/207.15 |
| 4,327,720 | 5/1982 | Bronson et al. | 128/911 |
| 4,351,330 | 9/1982 | Scarberry | 128/207.15 |
| 4,383,534 | 5/1983 | Peters | 128/207.15 |
| 4,607,643 | 8/1986 | Bell et al. | 128/207.15 |
| 4,917,107 | 4/1990 | Bell et al. | 128/715 |

Primary Examiner—Aaron J. Lewis
Attorney, Agent, or Firm—Krass & Young

[57]     ABSTRACT

A stethoscopic device for use with an endotracheal tube of the type adapted to be inserted through the mouth cavity of a surgery patient and into the trachea of the patient to position the outer end of the tube exteriorially of the patient's mouth and position the inner end of the tube proximate the patient's lungs to facilitate the delivery of anesthesia through the tube to the patient's lungs and/or to facilitate the delivery of a gaseous substance from a breathing machine through the tube to the patient's lungs during the surgical procedure. The invention devide includes a tube member adapted to be fitted at one end thereof in the outer end of the endotractheal tube and fitted at the other end thereof to a breathing tube leading to the anesthesia/breathing machine and a drum member positioned radially of the tube member and defining a membrane communicating with an aperture in the side wall of the tube member. The drum member further defines a chamber radially outwardly of the membrane and a fitting in the side wall of the drum member is adapted to be connected to the hose of an aural stethoscope so that the attending medical person may readily monitor the nature and frequency of the breath sounds emitted by the patient during the anesthesia/surgical procedure.

21 Claims, 1 Drawing Sheet

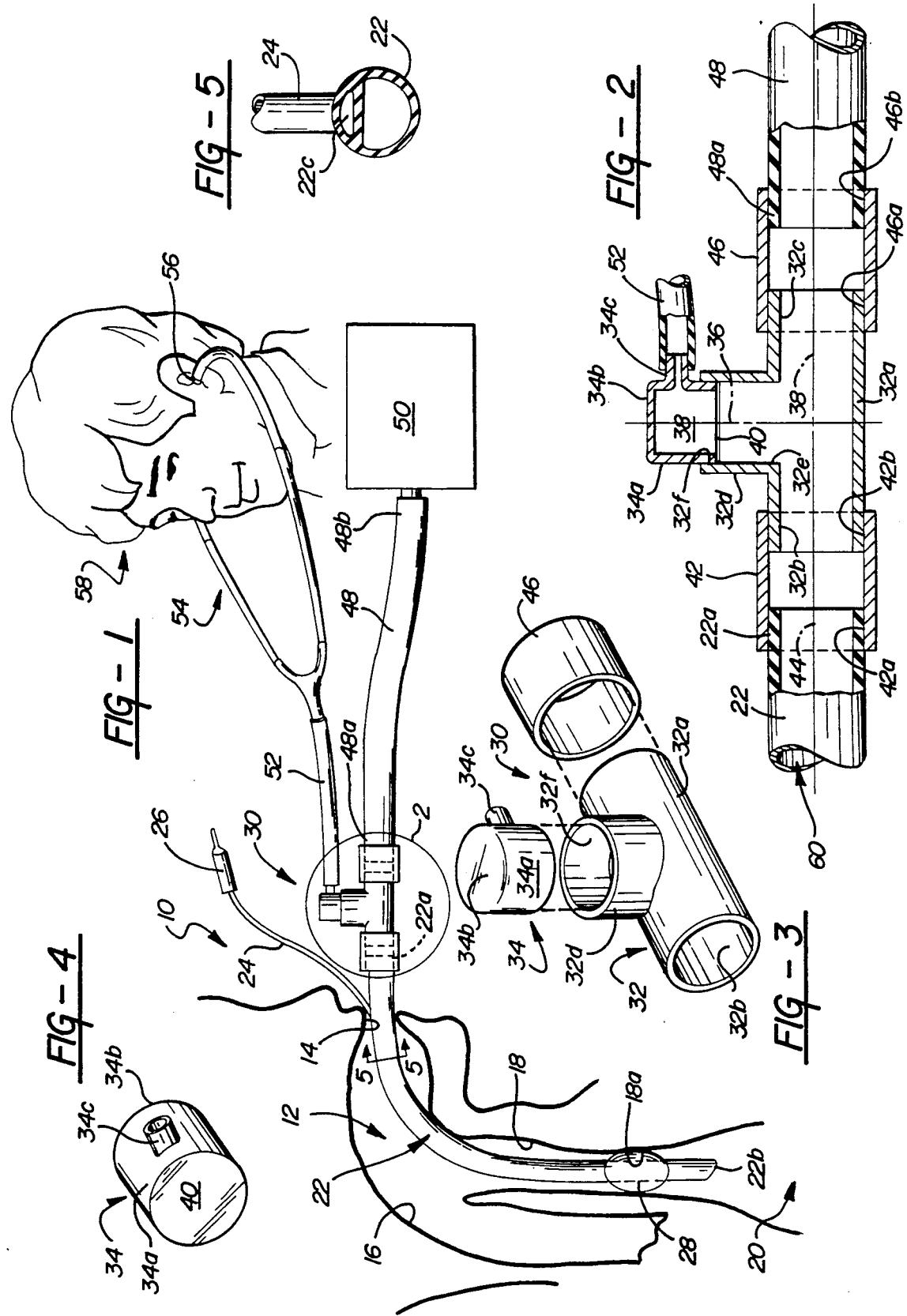

ENDOTRACHEAL STETHOSCOPE

BACKGROUND OF THE INVENTION

This invention relates to stethoscopes and more particularly to a device for monitoring the breathing sounds of a patient during an anesthetic or surgical procedure employing an endotracheal tube.

Endotracheal tubes are in common use during anesthetic and/or surgical procedures to administer an anesthetic to the patient and/or deliver a gaseous mixture to the patient to facilitate breathing during the surgical procedure. The endotracheal tube has a generally rigid arcuate configuration and is adapted to be inserted through the mouth cavity of the patient and into the trachea of the patient to position the outer end of the tube exteriorally of the patient's mouth and position the inner end of the tube proximate the patient's lungs so that anesthesia and/or a breathing mixture may be delivered to the patient's lungs through the endotracheal tube. It is important that the pulmonary breath sounds of the patient be monitored during the surgical procedure. In the prior art, the pulmonary breath sounds have been monitored by either an esophageal stethoscope (a stethoscopic tube inserted into the esophagus of the patient) or by a tube incorporated in the endotracheal tube and including a fitting for connection to the hose of a conventional aural stethoscope. Whereas these prior art arrangements for monitoring pulmonary breath sounds during a surgical procedure have been generally satisfactory, they have proven to be somewhat cumbersome in actual use and are also relatively expensive.

SUMMARY OF THE INVENTION

This invention is directed to the provision of an improved stethoscopic device for monitoring pulmonary breathing sounds during a surgical or anesthetic procedure.

More particularly, this invention is directed to the provision of an improved device for monitoring pulmonary breathing sounds during a surgical or anesthetic procedure involving the use of an endotracheal tube.

The invention device is intended for use with an endotracheal tube of the type adapted to be inserted through the mouth cavity of a surgery patient and into the trachea of the patient to position the outer end of the tube exteriorally of the patient's mouth and position the inner end of the tube proximate the patient's lungs to facilitate the delivery of anesthesia through the tube to the patient's lungs and to facilitate the delivery of a gaseous substance from a breathing machine through the tube to the patient's lungs during the surgical procedure.

The invention device includes means defining a membrane proximate the outer end of the endotracheal tube and means defining a fitting for connection to a conventional aural stethoscope. This arrangement provides an effective, convenient and inexpensive means of monitoring pulmonary breath sounds during a surgical procedure.

According to a further feature of the invention the membrane extends in a direction generally parallel to the central axis of the tube and is radially offset with respect to the tube axis. This specific orientation of the membrane allows it to effective sense the breathing sounds occurring in the endotracheal tube.

According to a further feature of the invention, the device further includes means defining a chamber enclosed at one end by the membrane, and the fitting opens into the chamber. This specific arrangement allows the chamber to amplify the sounds sensed by the membrane and allows the amplified sounds to be transmitted to the hose of the stethoscope through the fitting communicating with the chamber.

According to a further feature of the invention, the device includes a tube member adapted to fitted at one end thereof in the outer end of the endotracheal tube with the central axis of the tube member generally coaxial with the central axis of the endotracheal tube. This specific arrangement facilitates the provision of a smooth uninterrupted passage through the stethoscopic device for delivery of anesthesia and/or a breathing mixture.

According to a further feature of the invention, the tube includes an aperture in the side wall thereof between the ends thereof and the membrane is exposed at one side thereof to the aperture and at the other side thereof to the chamber. This specific arrangement provides a simple construction to effectively monitor the breath sounds appearing in the endotracheal tube.

According to a further feature of the invention, the device includes a drum member positioned radially of the tube member and defining the membrane and the chamber. The central axis of the drum member is generally normal to the central axis of the tube member and the membrane is defined at the radially inner end of the drum member. The drum member may be formed as a separate piece from the tube member or the drum member and tube member may be formed in an integral manner. This specific tube member/drum member construction provides an effective and inexpensive means of effectively monitoring the breath sounds occurring in the endotracheal tube.

In the disclosed embodiment of the invention, the radially outer end of the drum member comprises a solid end wall, the fitting for connection to the aural stethoscope is defined in the side wall of the drum member, and the other end of the tube member is adapted to be fitted to a breathing tube communicating with a breathing machine and/or an anesthetic machine. This specific constructional arrangement allows anesthesia and/or a breathing gaseous mixture to be delivered from the anesthesia machine/breathing machine to the endotracheal tube for transmittal to the lungs of the patient and provides a simple and effective means of monitoring the breathing sounds occurring in the endotracheal tube and transmitting these sounds to a conventional aural stethoscope.

BRIEF DESCRIPTION OF THE DRAWINGS

FIG. 1 is a schematic somewhat simplified view of an endotracheal apparatus incorporating the invention;

FIG. 2 is a detailed view taken within the circle 2 of FIG. 1;

FIG. 3 is an exploded perspective view showing portions of the invention stethoscopic device;

FIG. 4 is a perspective view of a portion of the invention stethoscopic device; and FIG. 5 is a cross-sectional view taken on line 5—5 of FIG. 1.

DETAILED DESCRIPTION OF THE PREFERRED EMBODIMENT

The invention endotracheal stethoscope is illustrated in FIG. 1 in association with a patient 10 undergoing an anesthetic and/or surgical procedure. The patient is shown as having a mouth cavity 12, a mouth opening 14, an esophagus 16, and a trachea 18 extending between mouth cavity 12 and lungs 20.

An arcuate endotracheal plastic tube 22 of known form is shown inserted through the mouth cavity 12 and into the trachea 18 to position the outer end 22a of the endotracheal tube exteriorally of the mouth opening 14 and position the inner end 22b of the endotracheal tube proximate the upper extremities of the lungs 20. A flexible plastic tube 24 communicates with an auxiliary passage 22c defined along the length of endotracheal tube 22 so that air supplied to tube 24 through a fitting 26 has the effect of inflating a plastic balloon 28 formed around and proximate the inner end of the tube to form an airtight seal at the interface 18a between the trachea and the balloon 28 and thereby preclude the escape of anesthesia and/or air from the lungs around the tube 22.

A stethoscopic device 30 according to the invention is adapted to be positioned at the outer end 22a of endotracheal tube 22. Device 30 includes a housing structure comprising a tube member 32 and a drum member 34, both preferably formed of a rigid plastic material.

Tube member 32 includes a cylindrical main body portion 32a defining a first open end or fitting 32b and a second open end 32c. Main body portion 32a has an inner diameter generally corresponding to the inner diameter or endotracheal tube passages 60 of endotracheal tube 22.

Member 32 further includes an annular cylindrical fitting portion 32d having a central axis 36 extending generally at right angles to the central axis 38 of tube member main body portion 32a and communicating with the interior of main body portion 32a through an aperture 32e defined in the side wall of main body portion 32a intermediate ends 32b, 32c.

Drum member 34 is sized to fit snugly and telescopically within the open upper end 32f of fitting portion 32d and includes a cylindrical side wall 34a, a solid circular upper end wall 34b, and a fitting 34c opening in side wall 34a. A thin flexible membrane 40 is stretched tightly across the lower end of drum member 34 and may either be formed integrally with the rigid portions 34a, 34b of member 34 or may be formed as a separate membrane which is thereafter suitable secured to the lower end of the rigid side wall 34a to provide a membrane enclosing the lower end of the drum member.

Drum member 34 is suitably rigidly fastened to tube member 32 as for example by fusing, sonic welding, or the like.

Tube member 32 is secured to the outer end 22a of endotracheal tube 22 by the use of a connector 42 including a first open end 42a into which endotracheal tube outer end 22a is inserted and a second end 40b into which one end of tube member main body portion 32a is inserted so as to position tube member main body portion 32a with its central axis or passage 38 in coaxial alignment with the central axis 44 of endotracheal tube 22. The endotracheal tube and the tube member 32 may be fitted into connector 42 with a press fit or may, alternatively, be provided with coacting screw threads.

The other end 32c of tube member main body portion 32a is fitted into one end 46a of a tubular connector 46 and a tube or hose 48 is fitted at one end 48a into the other open end 46b of connector 46. As with the connector 42, the connection between connector 46 and tube member main body portion 32a, and the connection between connector 46 and tube 48, may comprise a press fit connection or, alternatively, may comprise a threaded connection.

The other end 48b of tube 48 is connected to an anesthesia/breathing machine 50 of conventional form. As is known, machine 50 may comprise separate anesthesia and breathing machines or may comprise a single combined anesthesia and breathing machine. It will seen that tube 48, tube member 32, and endotracheal tube 22 are combined to define a continuous uninterrupted passage extending from the anesthesia/breathing machine 50 to the lungs 20 of the patient to facilitate the delivery of anesthesia from the machine 50 to the lungs of the patient and to facilitate the delivery of a gaseous mixture to the lungs of the patient during a surgical procedure to provide artificial breathing for the patient during the surgical procedure.

The rubber hose 52 of a conventual aural stethoscope 54 is fitted at one end thereof onto fitting 34c of drum member 34 and the ear pieces 56 of the stethoscope are inserted in known manner in the ears of the medical person 58 supervising the administration of the anesthesia and/or gaseous breathing mixture.

The illustrated apparatus not only facilitates the delivery of anesthesia/breathing gas to the patient during an anesthetic/surgical procedure, but also provides a ready, effective, and convenient means of monitoring the pulmonary breath sounds emitted by the patient during the procedure.

Specifically, the pulmonary breath sounds are transmitted by endotracheal tube 22 from the patient's lungs to the outer end 22a of the tube where they enter the main body portion 32a of tube member 32 for sensing by membrane 36, amplification by chamber 38, and subsequent transmittal through fitting 34 to hose 52 for transmittal to ear pieces 56 inserted in the ears of the medical person 58 so that the medical person is constantly apprised of the occurrence and the pattern of the breath sounds being generated by the patient. It will be understood that, in addition to monitoring the nature and frequency of the breath sounds, device 30 further confirms that the endotracheal tube 22 is in fact positioned properly in the trachea and further functions to detect bronchial spasms occurring during the anesthetic/surgical procedure.

The invention stethoscopic device will be seen to provide an effective and inexpensive means for monitoring the pulmonary breath sounds emitted by a patient during an endotracheal anesthetic/surgical procedure. Since the invention device may be produced at a very low cost it may be discarded after each use along with the endotracheal tube.

Whereas a preferred embodiment of the invention has been illustrated and described in detail it will be apparent that various changes may be made in the disclosed in the enclosed embodiment without departing from the scope or spirit of the invention.

I claim:

1. A stethoscopic device in combination with an endotracheal tube including a passage and having an outer end and an inner end and adapted to be inserted through the mouth cavity of a surgery patient and into the trachea of the patient to position the outer end of the tube exteriorly of the patient's mouth and position the inner end of the tube proximate the patient's lungs to facilitate the delivery of anesthesia through the tube to the patient's lungs and/or to facilitate the delivery of a gaseous substance from a breathing machine through the tube to the patient's lungs during the surgical procedure, said device comprising:
- a housing;
- a fitting on said housing sized and configured for connection to a stethoscope;
- a fitting on said housing sized and configured for connection to the outer end of the endotracheal tube;
- means defining a passage extending within said housing from the fitting for connection to the stethoscope to said endotracheal tube fitting; and forming an extension of the endotracheal tube passage, and
- a membrane extending across and blocking said passage at a location spaced from both fittings.

2. A stethoscopic device according to claim 1 wherein:
said membrane extends in a direction generally parallel to the central axis of said tube and is radially offset with respect to said axis.

3. A stethoscopic device according to claim 2 wherein:
said membrane includes opposed sides;
the portion of said passage on the stethoscope's fitting side of said membrane defines a chamber closed by one side of said membrane; and
said stethoscope fitting opens into said chamber.

4. A stethoscopic device for use with an endotracheal tube having an outer end and an inner end and adapted to be inserted through the mouth cavity of a surgery patient and into the trachea of the patient to position the outer end of the tube exteriorly of the patient's mouth and position the inner end of the tube proximate the patient's lungs to facilitate the delivery of anesthesia through the tube to the patient's lungs and/or to facilitate the delivery of a gaseous substance from a breathing machine through the tube to the patient's lungs during the surgical procedure, said device comprising:
- means defining a membrane proximate the outer end of the endotracheal tube extending in a direction generally parallel to the central axis of said tube and radially offset with respect to said axis and having opposed sides;
- means defining a chamber closed at one side by one side of said membrane;
- means defining a fitting for connection to a stethoscope opening into said chamber; and
- a tube member adapted to be fitting at one end thereof on the outer end of said endotracheal tube with the central axis of said tube member generally coaxial with the central axis of said endotracheal tube.

5. A stethoscopic device according to claim 4 wherein:
said tube includes an aperture in the side wall thereof between the ends thereof; and
the other side of said membrane is exposed to said aperture.

6. A stethoscopic device according to claim 5 wherein:
said chamber is defined radially outwardly of said membrane.

7. A stethoscopic device according to claim 6 wherein:
said device further includes a drum member positioned radially of said tube member and defining said membrane and said chamber.

8. A stethoscopic device according to claim 7 wherein:
said drum member is formed as a separate piece from said tube member and is secured to said tube member with said aperture in communication with said membrane.

9. A stethoscopic device according to claim 7 wherein:
the central axis of said drum member is generally normal to said central axis of said tube member; and
said membrane is defined proximate the radially inner end of said drum member.

10. A stethoscopic device according to claim 9 wherein:
the radially outer end of said drum member comprises a solid end wall; and
said fitting is defined in the side wall of said drum member.

11. A stethoscopic device according to claim 4 wherein:
said tube member is adapted to be fitted at its other end to a breathing tube connected to a breathing machine and/or an anesthetic machine.

12. An endotracheal apparatus comprising:
an endotracheal tube including a passage and having an outer end and an inner end and sized and configured to be passed through the mouth cavity of a surgery patient and into the trachea to position the outer end of the tube exteriorly of the patient's mouth and position the inner end of the tube proximate the patient's lungs to facilitate the delivery of anesthesia through the tube to the patient's lungs and/or to facilitate the delivery of a gaseous substance from a breathing machine through the tube to the patient's lungs during the surgical procedure; and
a stethoscopic device for detecting breathing sounds emitted by the patient and including a housing, a fitting on said housing sized and configured for connection to a stethoscope, a fitting on said housing sized and configured for connection in the outer end of the endotracheal tube, means defining a passage extending within said housing from the fitting for connection to the stethoscope to said endotracheal tube fitting and forming an extension of the endotracheal tube passage, and a membrane extending across and blocking said passage at a location spaced from both fittings.

13. An endotracheal apparatus according to claim 12 wherein:
said membrane is radially offset from the central axis of said endotracheal tube.

14. An endotracheal apparatus according to claim 13 wherein:
said housing includes an open ended tube adapted to be connected at one end thereof to said outer end of said endotracheal tube and adapted to be connected at the other end thereof to a tube connected to a breathing/anesthesia machine.

15. An endotracheal apparatus according to claim 14 wherein:
said tube includes an aperture in the wall thereof;
said housing further includes a drum positioned at one side of said tube proximate said aperture;
said membrane defines opposed sides, closes one end of said drum and communicates at one side thereof with said aperture; and
said drum defines a chamber on the other side of said member into which said stethoscope fitting opens.

16. An endotracheal apparatus comprising:

an endotracheal tube having an inner end and an outer end and sized and configured to be passed through the mouth cavity of surgery patient and into the trachea to position the outer end of the tube exteriorly of the patient's mouth and position the inner end of the tube proximate the patient's lungs;

first tube means extending from the outer end of said endotracheal tube to an anesthesia/breathing machine and forming a continuous uninterrupted passage with said endotracheal tube to facilitate the delivery of anesthesia/breathing gaseous substance through said tube means and said endotracheal tube to the lungs of the patient;

a membrane positioned along said first tube means in communication with said passage; and second tube means communicating at one end thereof with said membrane and adapted to be connected at its other end to a listening device whereby to monitor the breathing sounds of the patient.

17. An endotracheal apparatus according to claim 16 wherein:

said second tube means comprises the hose of an aural stethoscope.

18. An endotracheal apparatus according to claim 17 wherein:

said membrane defines opposed sides;

one side of said membrane communicates with said passage; and said apparatus further includes means defining a chamber on the other side of said membrane and a fitting communicating with said chamber and adapted to receive an end of said aural stethoscope hose.

19. A stethoscopic device for use in combination with an endotracheal tube having an inner end and an outer end, an anesthesia/breathing machine, and an aural stethoscope, said device comprising:

a tubular member adapted to be connected at one end thereof to the outer end of the endotracheal tube with said endotracheal tube inserted into the trachea of a surgery patient, said tubular member adapted to be connected at another end thereof to a tube connected with the anesthesia/breathing machine, and having an aperture in the side wall thereof between its ends;

a membrane, having opposed sides, positioned proximate said aperture and communicating at one side thereof with the interior of said tube member;

means defining a chamber at the other side of said membrane closed by said membrane; and a fitting communicating with said chamber and adapted to receive one end of the hose of the aural stethoscope.

20. A stethoscopic device according to claim 19 wherein:

said device includes a drum member rigid with said tube member, positioned with its central axis generally normal to the central axis of said tube member and aligned with said aperture, defining said membrane proximate the radially inner end thereof, and defining said chamber radially outwardly of said membrane.

21. An stethoscopic device according to claim 20 wherein:

the radially outer end of said drum comprises a solid end wall; and said fitting is provided in the side wall of said drum member.

* * * * *